United States Patent [19]
Cohen

[11] 4,183,358
[45] Jan. 15, 1980

[54] MALE CONTRACEPTIVE DEVICE

[76] Inventor: Milton J. Cohen, 9201 Persimmon Tree Rd., Potomac, Md. 20854

[21] Appl. No.: 825,239

[22] Filed: Aug. 17, 1977

[51] Int. Cl.² ............................................. A61F 5/42
[52] U.S. Cl. .................................................. 128/294
[58] Field of Search .................. 128/132 R, 294, 275, 128/275.1

[56] References Cited
U.S. PATENT DOCUMENTS

| | | | |
|---|---|---|---|
| 1,240,125 | 9/1917 | Doud | 128/294 |
| 2,291,191 | 7/1942 | Scudder | 128/294 |
| 3,463,141 | 8/1969 | Mozlof | 128/132 R |

Primary Examiner—Lawrence W. Trapp

[57] ABSTRACT

A male contraceptive device including a urethral sealing member in the form of a hollow tube having means adjacent one end thereof to engage the fossa navicularis within the urethra in a sealing relationship and a container mounted on the tube adapted to receive sperm passing from the urethra into the hollow tube.

6 Claims, 8 Drawing Figures

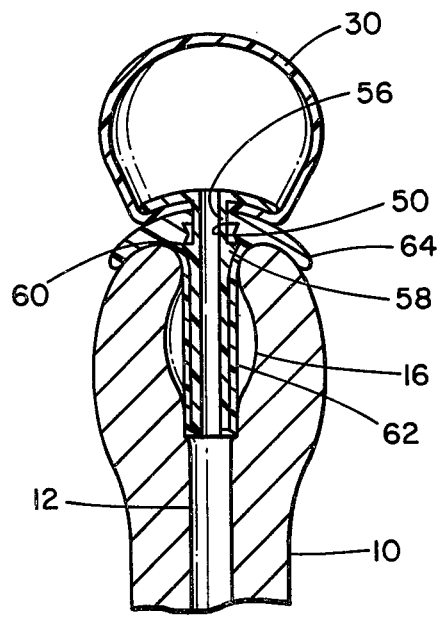
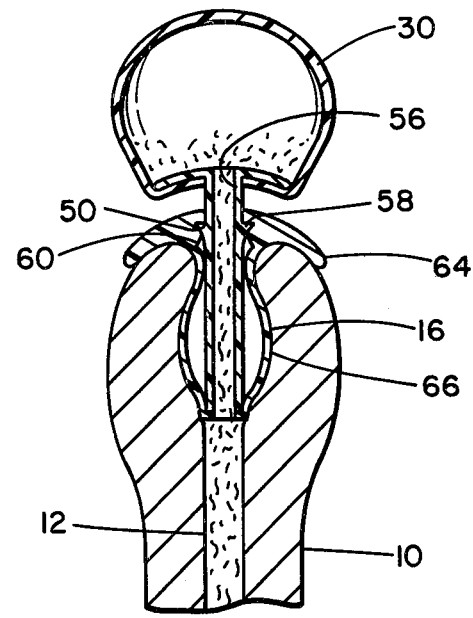
FIG.5  FIG.6
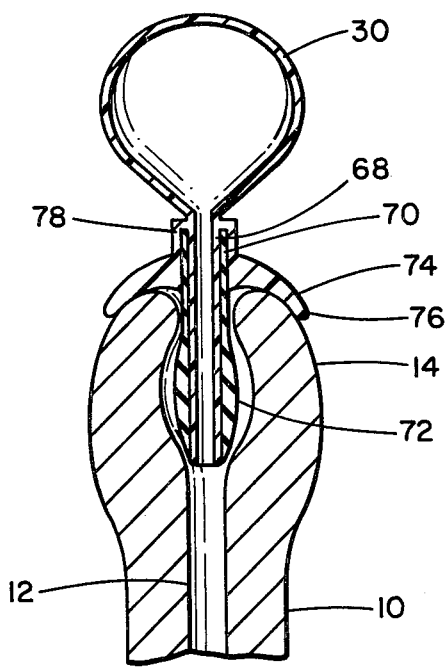
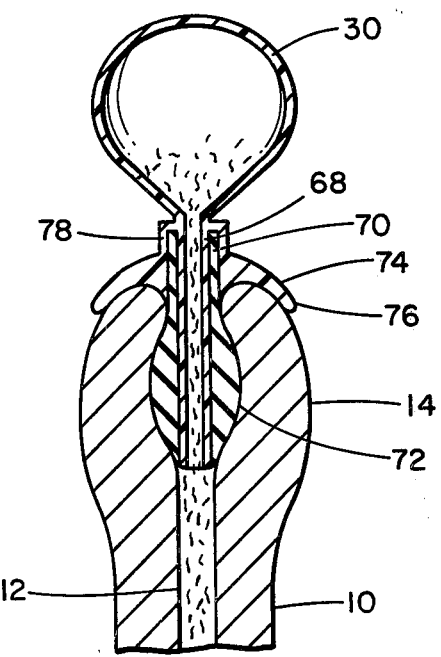
FIG.7  FIG.8

MALE CONTRACEPTIVE DEVICE

This invention relates to a contraceptive device, and more particularly to a contraceptive device for use in males.

There have been a number of attempts over many, many years to devise a completely acceptable method or device for birth control, i.e., the prevention of conception. These devices and/or methods, known in the art as contraceptives, include coitus interruptus (the original and oldest method for birth control), condoms, intra-uterine devices, the rhythm method, spermicidal foams and like chemicals, diaphragms and sterilizations, both for the male and female.

All of the foregoing have one or more serious drawback. However, due to a lack of a method or device more effective and less harmful to the user, the public and the medical profession have accepted the above devices and techniques as the leading methods for birth control. For example, coitus interruptus has been objectionable from a physical standpoint since it interferes with the normal ejaculation of the sperm, and can cause psychological and organic reactions. The "pill", on the other hand, though perhaps the most well-known and indeed the most widely used birth control method presently available, can cause adverse side effects such as vascular disturbances (i.e., phlebitis).

The condom is objectionable from the standpoint that it interferes with complete sensation normally received upon ejaculation by reason of the fact of its serving as a physical barrier to the penis. Intra-uterine devices, also presently in wide spread use, can cause physical disturbances in the female organs, and may not be 100% effective. Likewise ineffective is the rhythm method practiced by certain religious groups; it is at best a gamble.

Spermicidal foams and other chemicals inserted into the vaginal area can be harmful to the tissues therein and likewise suffer from the further disadvantage of not being 100% effective. Diaphragms present a like problem; unless inserted by a physician, the user may not position the device effectively. It has also been known to cause irritation in some women.

An even more controversial form of contraception is sterilization of either the male or female. That can frequently cause a psychological reaction in the form of remorse, regret or the like. In addition, that technique suffers from the further disadvantage of being irreversible.

Nearly all of the emphasis anent contraception has been laid at the foot of the female. The philosophy has been to permit the sperm to enter the vagina and then attempt to circumvent the entrance of the sperm to the uterus and thereby prevent impregnation of the female. The better approach is not to permit the entrance of the sperm into the female at all, but prevent the ingress of sperm to the vagina. The only accepted method embodying those considerations is the condom. But that, as has been pointed out above, is unsatisfactory because it prevents complete enjoyment of the sex act, both by the male and the female as well.

It is accordingly an object of the present invention to provide a birth control device which overcomes the foregoing disadvantages and which is capable of use by the male in a safe and effective manner.

It is a further object of the invention to provide a male contraceptive which is inexpensive to produce and use and simple to use and remove.

It is another object of the present invention to provide a male contraceptive device which can be effectively used to prevent the entrance of sperm to the vagina, without interference with physical sensations.

It is yet another object of the invention to provide a male contraceptive device which is simple to use, simple to actuate and simple to remove afterward, and yet is effective to prevent infection with venereal disease by sealing off the entrance into the penis during insertion into the vagina.

These and other objects and advantages of the invention will appear more fully hereinafter, and for purposes of illustration but not of limitation, embodiments of the invention are shown in the accompanying drawings wherein:

FIG. 5 is another embodiment of a male contraceptive device embodying the features of this invention;

FIG. 6 is a sectional view of the contraceptive device illustrated in FIG. 5 as it is being placed into the desired position in the penis;

FIG. 7 is a sectional view of another male contraceptive device embodying the features of this invention; and, FIG. 8 is a sectional view of the device illustrated in FIG. 7 when it is in position for use.

The concepts of the present invention reside in a male contraceptive device in which a container or bladder is secured to the penis by means of a flexible sleeve adapted to be received in a sealing relationship within the urethra. In that way, ejaculated sperm from the male enters the container or bladder and thus is prevented from entering the female to effect fertilization. The sperm bag is thus secured to the penis by reason of a natural anatomical deviation occurring in the urethra within the glans of the penis. That deviation, medically known as the fossa navicularis, is an annular depression within the urethra, and allows a flexible seal to be placed in the urethra while the seal is in a contracted state. After insertion, the seal expands to engage the fossa navicularis in a sealing relationship. Without the flexible seal, a straight tubular member inserted into the urethra could easily slip out by reason of the secretions produced by the body during intercourse which would serve to lubricate the surface between the tubular member and the walls of the urethra. In the practice of this invention, the male contraceptive device includes a flexible sealing member having a configuration corresponding to that of the fossa navicularis, and is thereby physically confined therein to prevent the urethra sealing member from slipping from the urethra, notwithstanding the lubrication provided by the body organs. In this way, it is possible to attach a container or bladder for receiving sperm without covering the glans, the center of physical sensation.

Figure 1:
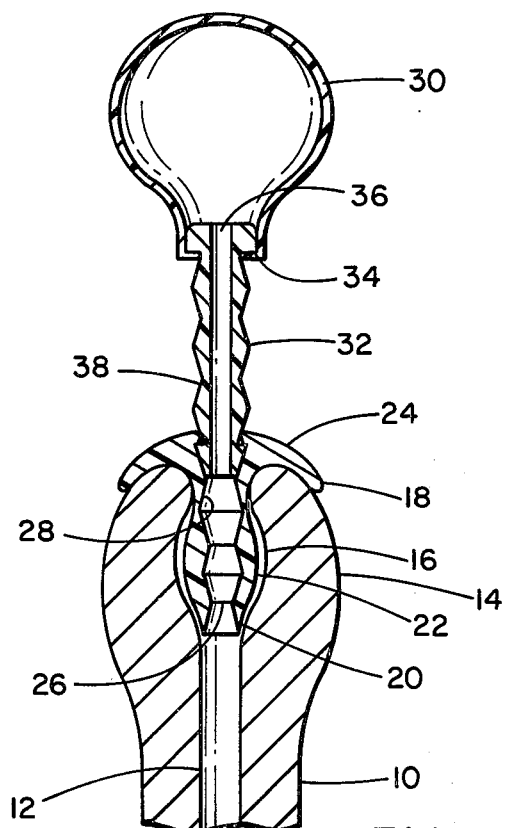
FIG. 1 is a sectional view of a birth control device embodying the features of this innvention as it is being readied for use with the penis.
Figure 2:
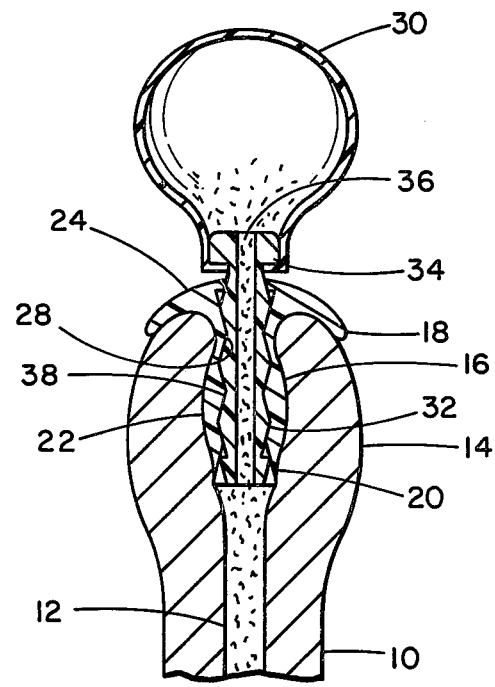
FIG. 2 is a sectional view of the embodiment shown in FIG. 1 as it is inserted in the penis and ready for use.

Referring now to the drawings, there is shown in FIGS. 1 and 2 one embodiment of the present invention. As is shown in these figures, the penis is generally shown as 10, and includes a central passage, medically known as the urethra, 12, extending thereto. The enlarged or head portion of the penis, the glans 14, locates the position of the fossa navicularis, the annular concave indentation 16 within the urethra and within the glans.

The contraceptive device of this invention includes a generally T-shaped urethral sealing member 18 including an elongate portion 20 adapted to be inserted in the urethra. It is an important concept of this invention that the elongate portion 20 includes a flexible convex annular portion 22 having a configuration corresponding to the annular concave configuration of the fossa navicularis 16. The urethral sealing member 18 also includes a disc member 24 integral with the elongate portion 20, the disc portion being adapted to overlay only the glans adjacent the entrance to the urethra. Both the elongate portion 20 and the disc portion 24 define a central opening 26 communicating with the urethra.

In the embodiment shown in FIGS. 1 and 2, the central opening 26 includes a female threaded portion 28.

The contraceptive device of this invention also includes container means 30 mounted on a tubular member 32. As shown in FIGS. 1 and 2 of the drawing, the container means 30 is fitted in a sealing relationship about a lip 34 of the tubular member 32. That tubular member 32 defines a central opening 36 extending therethrough and communicating with the interior of the container means 30. It also defines, about its outer periphery, male threads 38 adapted to threadably engage the female threads 28 of the urethral sealing member 18, and specifically the elongate portion 20.

As shown in these figures, the container means 30 mounted on the tubular member 32 is thus inserted into the elongate portion 20 of the urethral sealing member 18 to threadably engage the elongate portion 20. In this position, the central opening 26 of the elongate portion 20 communicates with the central opening 36 of the tubular portion 32 which in turn communicates with the container means 30 so that sperm passing through the urethra 12 pass directly into the container means 30.

A secure sealing relationship between the elongate portion 20 and the urethra is established by reason of the expansion of the elongate portion 20 as the tubular portion 32 is threadably engaged with the female threads 28 of the elongate portion 20. Thus, the threadable engagement of the tubular portion 32 with the elongate portion 20 causes expansion of the tubular portion 20 so that the annular convex portion 22 of the elongate portion 20 expands to securely grip the fossa navicularis, as is perhaps most clearly shown in FIG. 2 of the drawing.

In use, the urethral sealing member 18 is positioned such that the elongate portion 20 is inserted into the urethra and the disc member 24 is in contact with the glans immediately adjacent the opening of the urethra. In this position, as shown in FIG. 1, the flexible elongate portion 20 is in the relaxed position, thus leaving a space between the convex portion 22 of the elongate portion 20 and the fossa navicularis 16. Then, the tubular member 32, with the container means 30 fixed thereon, is threadably engaged with the urethral sealing member 18 to expand the elongate portion 20 thereof and engage the convex portion 22 with the fossa navicularis in a sealing relationship.

After use, the procedure described above is reversed. As soon as the tubular member 32 is removed from the urethral sealing member 18, the elongate portion 20 is again relaxed, thus permitting withdrawal of the elongate portion 20 from the urethra.

Figure 3:
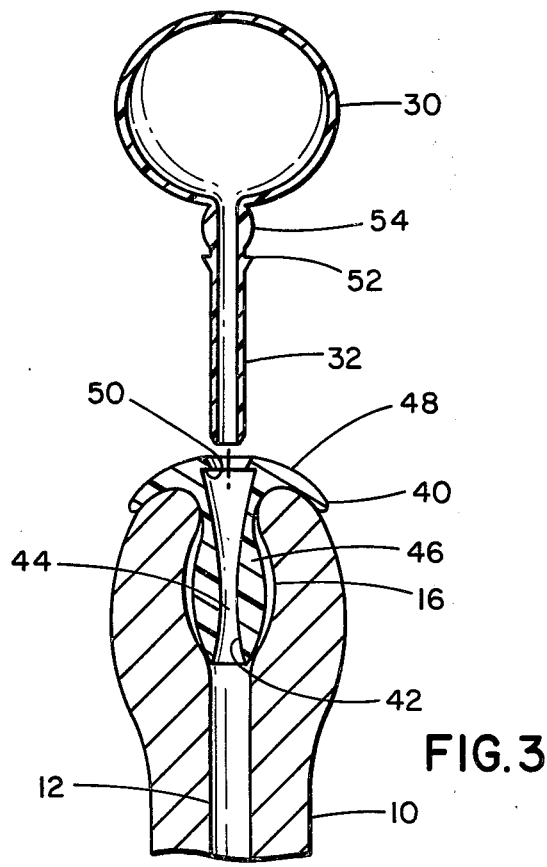
FIG. 3 is another embodiment of a male contraceptive device, illustrating how the device is inserted into the penis.
Figure 4:
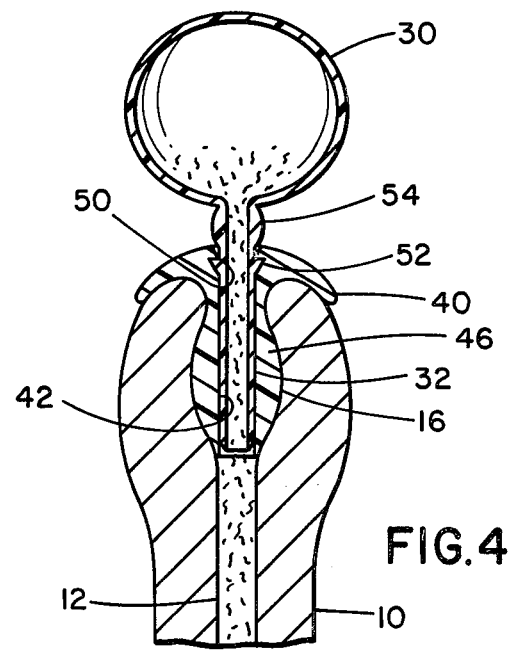
FIG. 4 is a sectional view of the embodiment of FIG. 3 in position for use.

Another embodiment of the invention is shown in FIGS. 3 and 4 of the drawing. In this embodiment, the urethral sealing member 40 is modified such that the interior surfaces 42 of the central opening 44 are relatively smooth, elastic members. In their relaxed state, as shown in FIG. 3, the convex portion 46 extends away from the fossa navicularis 16. When the tubular member 32, carrying the container means 30 is affixed, is inserted into the central opening 44, the convex portion 46 is expanded toward a sealing relationship with the fossa navicularis as shown in FIG. 4.

To secure the tubular member 32 in the central opening 44, it is desirable to provide the disc portion 48 with an annular locking lip 50 adapted to engage a corresponding annular locking flange 52 on the tubular member 32. To facilitate insertion of the tubular member 32 into the central opening 44 of the urethral sealing member 40, the tubular member 32 also includes an area of enlarged cross section 54 adjacent the container means 30. By squeezing the enlarged cross section 54, the lower portion of the tubular member 32 is squeezed together to facilitate insertion of the tubular member 32 into the central opening 46. As will be appreciated by those skilled in the art, once the tubular member 32 has been inserted into the central opening 44, with the locking lip 50 in engagement with the locking flange 52, the tubular member 32 carrying the container means 30 cannot be removed from the urethral sealing member. When it is desired to remove the device, the enlarged cross section 54 is compressed to disengage the locking relationship between the lip 50 and the flange 52 to permit the tubular member 32 to be withdrawn. Then, the elongate portion 46 of the urethral sealing member is in the relaxed state and can be withdrawn from the urethra.

A variation of the embodiment shown in FIGS. 3 and 4 is illustrated in FIGS. 5 and 6. In this embodiment, the tubular member 56 is a rigid material, such as a rigid plastic tube on which there is mounted the container means 30 at one end. Positioned intermediate on the tubular member 56 in an outwardly projecting locking flange 58 adapted to engage a corresponding locking lip 60 carried on the elongate portion 62 of the urethral sealing member 64. As is perhaps most clearly shown in FIG. 5 of the drawing, when the locking flange 58 is engaged with the locking lip 60, the elongate portion 62 is under tension, and thus has a cross section generally corresponding to the cylindrical cross section of the tubular member 56. Then, as the flange 58 is released from the locking lip 60, the tubular member 56 is displaced in a direction outwardly from the urethra so that the locking flange 58 engages the annular locking lip 50. The partial withdrawal of the tubular member 56 from the urethral sealing member releases the tension on the urethral sealing member, thus permitting the latter to expand outwardly to form an annular portion 66 which engages in a sealing relationship with the fossa navicularis to secure the urethral sealing member in the desired position as shown in FIG. 6.

After use, the contraceptive device is removed by advancing the tubular member 56 into the urethra to subject the elongate 62 to tension, thus removing the bowed-out configuration creating the concave projection 66. Once the elongate portion 62 has been subjected to tension, the urethral sealing member can then be withdrawn from the urethra.

Another embodiment of the invention is shown in FIGS. 7 and 8 of the drawing. In this embodiment, the contraceptive device includes a tubular member 68 which carries the container means 30. That tubular member 68 is enveloped by an elongate sleeve 70 having a convex portion 72 opposite the container means 30. As is shown in these figures, the elongate tube 68 and the sleeve 70 are secured together by means of the urethral sealing member 74 including a disc portion 76 and a neck 78. In this embodiment, the annular convex portion 72 of the sleeve 70 is released by means of pressure applied to the neck 78, forcing partial collapse of the tubular member 68 and the sleeve 70. When the pressure on the neck 78 is released, the tubular member 68 and the sleeve 70 expand radially so that the annular convex portion 72 of the sleeve 70 expands toward a sealing relationship of the fossa navicularis, thus securing the device in position.

It will be understood that various changes and modifications can be made in the details of construction and use without departing from the spirit of the invention, especially as defined in the following claims.

I claim:

1. A male contraceptive device comprising:
   (a) a urethral sealing member in the form of an elongate hollow tube adapted to be received in a urethra and communicating with the urethra, said tube having, adjacent one end thereof, means to engage the fossa navicularis, said means including a flexible convex annular portion adapted to be displaced outwardly to engage the fossa navicularis in a sealing relationship, and
   (b) container means mounted on said tube adapted to receive sperm passing from the urethra, said container means being mounted on a threaded member and the interior of said tube defining threads adapted to receive said threaded member whereby the threadable tubular member with said tube serves to expand the flexible convex portion of said tube to effect a sealing relationship between said tube and the fossa navicularis.

2. A male contraceptive device comprising:
   (a) a urethral sealing member in the form of an elongate hollow tube adapted to be received in a urethra and communicating with the urethra, said tube having, adjacent one end thereof, means to engage the fossa navicularis in a sealing relation, and
   (b) container means mounted on said tube adapted to receive sperm passing from the urethra, said container means including a sleeve member adapted to be received within the said elongate hollow tube whereby pressure on the neck of said sleeve operates to collapse the urethral sealing member and the release of pressure on the neck operates to relax the urethral sealing member to form a sealing relationship with the fossa navicularis.

3. A male contraceptive device comprising a urethral sealing member in the form of an elongate hollow tube adapted to be received in a urethra and communicating with the urethra, said tube having, adjacent one end thereof, means to engage the fossa navicularis in a sealing relation, container means mounted on said tube adapted to receive sperm passing from the urethra, said means to engage the fossa navicularis including a flexible convex annular portion adapted to be displaced outwardly to engage the fossa navicularis in a sealing relationship, and the urethral sealing member including an annular locking lip and said container means including an elongate tubular portion having a locking flange adapted to engage the locking lip to secure the container means with the urethral sealing member.

4. A device as defined in claim 3 wherein the inner diameter of the urethral sealing member is reduced in the area adjacent to the annular portion of the sealing means so that the insertion of the elongate tubular portion of the container means in the urethral sealing member will forceably expand the annular portion and thereby displace it outwardly to engage the fossa navicularis in a sealing relationship.

5. A device as defined in claim 3 wherein the container means includes a rigid tubular member adapted to insert in said elongate hollow tube whereby the rigid tubular member operates to create tension on the hollow tube and the release of said tubular member within the urethral sealing member operates to relax the urethral sealing member and thereby create a seal between the urethral sealing member and the fossa navicularis.

6. A male contraceptive device comprising:
   (a) a urethral sealing member in the form of an elongate hollow tube adapted to be received in a urethra and communicating with the urethra, said tube having, adjacent one end thereof, means to engage the fossa navicularis in a sealing relation, and a disc portion integral with said tube, said disc portion adapted to overlay the glans to prevent displacement of the hollow tube into the urethra, and
   (b) container means mounted on said tube adapted to receive sperm passing from the urethra.

* * * * *